(12) United States Patent
Rumpf

(10) Patent No.: US 11,911,427 B2
(45) Date of Patent: Feb. 27, 2024

(54) EXTRACTION AND INFUSION OF ACTIVE COMPONENTS FROM PLANT MATERIALS

(71) Applicant: Wilhelm Rumpf, Vicksburg, MI (US)

(72) Inventor: Wilhelm Rumpf, Vicksburg, MI (US)

(*) Notice: Subject to any disclaimer, the term of this patent is extended or adjusted under 35 U.S.C. 154(b) by 0 days.

(21) Appl. No.: 17/740,416

(22) Filed: May 10, 2022

(65) Prior Publication Data

US 2023/0285482 A1 Sep. 14, 2023

Related U.S. Application Data

(60) Provisional application No. 63/319,298, filed on Mar. 12, 2022.

(51) Int. Cl.
*A61K 36/185* (2006.01)

(52) U.S. Cl.
CPC ........ *A61K 36/185* (2013.01); *A61K 2236/31* (2013.01); *A61K 2236/35* (2013.01); *A61K 2236/37* (2013.01); *A61K 2236/55* (2013.01)

(58) Field of Classification Search
None
See application file for complete search history.

(56) References Cited

U.S. PATENT DOCUMENTS

| | | |
|---|---|---|
| 2016/0346339 A1 | 12/2016 | Finley et al. |
| 2018/0125980 A1 | 5/2018 | Finley et al. |
| 2018/0344661 A1 | 12/2018 | Finley et al. |
| 2019/0231833 A1 | 8/2019 | Garti et al. |
| 2019/0336521 A1 | 11/2019 | Kotra et al. |
| 2020/0054701 A1 | 2/2020 | Finley et al. |
| 2020/0215026 A1 | 7/2020 | Blackmon et al. |
| 2020/0330378 A1 | 10/2020 | Friedman |
| 2021/0052512 A1 | 2/2021 | Guy et al. |
| 2021/0292295 A1 | 9/2021 | Aizikovich |
| 2021/0309629 A1 | 10/2021 | Durst et al. |
| 2022/0008839 A1* | 1/2022 | Jackson ................ G01N 11/00 |

* cited by examiner

*Primary Examiner* — Michael V Meller

(74) *Attorney, Agent, or Firm* — Jenei LLC

(57) ABSTRACT

The present invention relates to methods of extracting cannabinoids from cannabis. Also provided is a cannabinoid extract produced by the method of the invention. In one aspect of the present invention, there is provided a method of preparing a cannabinoid extract, the method comprising heating cannabis plant material for an appropriate time and temperature in order to substantially decarboxylate the cannabis plant material; (ii) extracting cannabinoids from the decarboxylated cannabis plant material by the use of solvents; and (iii) infusing lipid with the extracted cannabinoids. In one embodiment, the present invention provides for methods of preparing a cannabinoid-infused lipid composition and products made by such methods. In another embodiment, the methods render the normally unpleasant tasting concentrated cannabis oil flavorless or reduced in unpleasantness.

8 Claims, No Drawings

EXTRACTION AND INFUSION OF ACTIVE COMPONENTS FROM PLANT MATERIALS

CROSS-REFERENCE TO RELATED APPLICATIONS

This application is a U.S. Nonprovisional Patent Application, which claims the benefit to U.S. Provisional Patent Application Ser. No. 62/502,865 entitled "EXTRACTION AND INFUSION OF ACTIVE COMPONENTS FROM PLANT MATERIALS", filed Mar. 12, 2022, the contents of which are hereby incorporated by reference in their entirety for any purpose.

BACKGROUND OF THE INVENTION

1. Field of the Invention

The field of art disclosed herein pertains to methods of extraction and infusion of CBD and THC into lipid compounds.

2. Description of the Related Art

Cannabis and cannabis-derived products have had a long history of medicinal use including use as an anticonvulsant, sedative, hypnotic, anti-depressant, analgesic, anti-inflammatory, anti-emetic, anti-spasmodic, and appetite-stimulator. The main medically active chemical compounds in cannabis are the phytocannabinoids (referred herein simply as cannabinoids). Plants in the genus Cannabis are unique in that they produce five cannabinoids enzymatically in their trichomes: cannabigerolic acid (CBGA; CAS 25555-57-1), cannabinerolic acid (CBRA; CAS 165134-19-0), $\Delta^9$-tetrahydrocannabinolic acid (THCA; CAS 23978-85-0), cannabidiolic acid (CBDA; CAS 1244-58-2) and cannabichromenic acid (CBCA; CAS 185505-15-1). All of these exist predominantly in their pentyl-tail versions (C5; olivetols) but can also be found in their heptyl-(C7; phorols), propyl-(C3; varinols) and methyl-($C_1$; orcinols) versions depending on the phenolic precursor that generated the CBGA or CBRA.

Many other cannabinoids can arise from this core group via non-enzymatic pathways. Best known and most significant is decarboxylation, but these can also involve slower pathways like dehydrogenation, oxygenation, hydroxylation, glycosylation, and isomerization driven by acid or ultra-violet light. The most renowned of these non-enzymatic derivatives are $\Delta^9$-tetrahydrocannabinol (THC; CAS 1972-08-3), cannabinol (CBN; CAS 521-35-7) and cannabidiol (CBD; CAS 13956-29-1). Cannabis trichomes also produce terpenoids but these are not unique to cannabis and are widespread in plants.

A number of cannabinoid-based pharmaceuticals have been approved for use in management of pain associated with multiple sclerosis and cancer, to treat poor appetite, nausea, sleep apnea, HIV/AIDS induced anorexia and chemotherapy induced nausea and vomiting. A CBD drug has also been approved to treat severe forms of epilepsy. CBD has also been shown to have anti-inflammatory properties that are potentially useful in the treatment of symptoms of arthritis.

Cannabinoids have previously been separated from the plant by extraction with organic solvents including hydrocarbons and alcohols. The solvents are flammable and many are toxic. Other extraction techniques are known in the art including the method disclosed in WO2020028991.

U.S. Pat. No. 9,732,009B2 teaches purifying a cannabinoid from dried cannabis, powdered cannabis, chopped cannabis, or ground cannabis with canola oil, tributylmethylammonium methyl sulfate, or 1-butyl-3-methylimidazolium chloride.

Most large-scale processing of cannabis to produce cannabinoids generally uses extraction by ethanol or supercritical carbon dioxide, sometimes in combination. These processing methods require that the cannabis be dried and usually dry-milled prior to extraction.

For formulating into pharmaceutical compositions, the cannabinoids are often extracted from the plant source by various methods.

One of the methods commonly used is extraction by carrier oils, in which the carrier oil is used as a solvent for the extraction of the cannabinoid species from the plant source. Since the oil-filled trichomes of the inflorescences are fat-soluble, natural plant oils are an effective way to extract the mixture of cannabinoid species from the cannabinoid-laden resin and other parts of plant.

Another method often used is extraction by organic solvents capable of dissolving cannabinoids. Such extraction requires tailoring of the solvent for effective extraction, and often results in low yields of extraction. Further, it is difficult to remove traces of the solvent from the end-product, reducing the degree of purity and the safety of the resulting extract. Most of these extractions are found to be insufficient and often leave undesired traces of the solvent (especially when petroleum ethers are used).

A further method which is used for obtaining extraction of various compounds from various plant sources is supercritical $CO_2$ extraction. In the $CO_2$ extraction process, $CO_2$ at super-critical conditions (i.e., high temperature and pressure) is used for extraction of the cannabinoid species. Although relatively effective for extracting a variety of compounds from the plant source, this technique is often more complicated, time consuming and very expensive compared to liquid extraction. In addition, this technique is far from being selective for specific cannabinoid and may concomitantly extract also various essential oils.

Although various methods exist for extraction of cannabinoids, these all have the common disadvantage of low extraction yield and low (or no) selectivity. Namely, the extraction methods known to date extract various species of cannabinoids from the plant source, often resulting in a mixture of various concentrations and ratios of CBD and THC, hindering subsequent formulation and use of CBD in pharmaceutical compositions.

SUMMARY OF THE INVENTION

An object of the present invention is to provide methods of extracting cannabinoids from cannabis. In accordance with another aspect of the invention, there is provided an Eat Bake Enjoy (EBE) Method of preparing a cannabinoid extract from cannabis plant material without excessive decarboxylation and infusion generated heavy organics, which carry over unpleasant flavors.

In accordance with another aspect of the invention, there is provided an edible, cannabinoid-infused lipid composition derived from cannabis plant material generated with a darker color due to increased amount of nondegraded chlorophyll.

In accordance with another aspect of the invention, there is provided a cannabinoid extract produced by the method of the invention.

In accordance with an aspect of the present invention, there is provided a method of preparing a cannabinoid extract, the method comprising heating cannabis plant material for an appropriate time and temperature in order to substantially decarboxylate the cannabis plant material; (ii) extracting cannabinoids from the decarboxylated cannabis plant material by the use of solvents; and (iii) infusing lipid with the extracted cannabinoids.

Another object and advantage of the present invention is to render the normally unpleasant tasting concentrated cannabis oil flavorless.

The present invention relates to methods of extraction and infusion of cannabinoids into lipid compounds. In one embodiment, the present invention provides for methods of preparing a cannabinoid-infused lipid composition and products made by such methods.

In another embodiment, the present invention includes a method of preparing a cannabinoid-infused lipid composition that renders the normally unpleasant tasting concentrated cannabis oil flavorless or reduced in unpleasantness.

The method comprises (i) heating cannabis plant material for an appropriate time and temperature in order to substantially decarboxylate the cannabis plant material; (ii) extracting cannabinoids from the decarboxylated cannabis plant material by the use of solvents; and (iii) infusing lipid with the cannabinoids. In some embodiments, steps (a) and (b) may be repeated at least once.

In one or more embodiments of the present invention, the method of preparing a botanical extract comprises (a) providing a cannabis plant material; (b) decarboxylation of the cannabis plant material by heating to convert cannabinoid acids present in the plant material to neutral cannabinoids (c) contacting an organic solvent with the decarboxylated cannabis plant material; (d) extracting at least one bioactive molecule from the decarboxylated cannabis plant material into the organic solvent, thereby producing an organic solvent comprising a botanical extract; (e) contacting the organic solvent comprising a botanical extract with a lipid compound; (f) infusing at least one bioactive molecule from the botanical extract material into the lipid compound, thereby producing a cannabinoid-infused lipid composition.

In another embodiment, the method of preparing a botanical extract comprises (a) providing a cannabis plant material; (b) decarboxylation of the cannabis plant material by heating the cannabis plant material to temperatures and for times which ensure at least 95% conversion of the acid cannabinoids from the acid form to their neutral form, while ensuring thermal degradation of THC to CBN is less than 10%; (c) contacting an organic solvent with the decarboxylated cannabis plant material; (d) extracting at least one bioactive molecule from the decarboxylated cannabis plant material into the organic solvent, thereby producing an organic solvent comprising a botanical extract; (e) contacting the organic solvent comprising a botanical extract with a lipid compound; (f) infusing at least one bioactive molecule from the botanical extract material into the lipid compound, thereby producing a cannabinoid-infused lipid composition; and (g) recovering the cannabinoid-infused lipid composition from the organic solvent; thereby producing an edible additive.

In another embodiment, the method of preparing a botanical extract comprises (a) providing a cannabis plant material; (b) decarboxylation of the cannabis plant material by heating the cannabis plant material to temperatures and for times which ensure (i) at least 90% conversion of the acid cannabinoids from the acid form to their neutral form, while ensuring thermal degradation of THC to CBN is less than 10% and (ii) and the cannabis plant material contains no more than 10% of moisture; (c) contacting an organic solvent with the decarboxylated cannabis plant material; (d) extracting at least one bioactive molecule from the decarboxylated cannabis plant material into the organic solvent, thereby producing an organic solvent comprising a botanical extract; (e) contacting the organic solvent comprising a botanical extract with a lipid compound; (f) infusing at least one bioactive molecule from the botanical extract material into the lipid compound, thereby producing a cannabinoid-infused lipid composition; and (g) recovering the cannabinoid-infused lipid composition from the organic solvent; thereby producing an edible additive.

In accordance with another aspect of the invention, there is provided a cannabinoid extract produced by the method of the invention. In one or more embodiments, the present invention provides for a product created in accordance with the present methods with such an improved product having a reduced perceived sensation of the normally unpleasant taste or cannabis oil.

In one or more embodiments, the cannabinoid-infused lipid composition of the present invention can be used (i) directly as a medicine, natural health product, food product, or for recreational use, or (ii) as a raw material in the preparation of products, such as pharmaceutical, natural health products, food products, or recreational use products for known uses of decarboxylated cannabinoid(s).

Another aspect of the invention is a food product comprising a cannabinoid-infused lipid composition or synthetic cannabinoid-derived composition of this invention such that the food comprises at least one cannabinoid.

DETAILED DESCRIPTION

Definitions

Listed below are definitions of various terms. These definitions apply to the terms as they are used throughout this specification, unless otherwise limited in specific instances, either individually or as part of a larger group.

As used in the specification and in the claims, the term "comprising" can include the aspects "consisting of" and "consisting essentially of."

As used in the specification and claims, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated +/−10% variation unless otherwise indicated or inferred. The term is intended to convey those similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

"Optional" or "optionally" means that the subsequently described event or circumstance may or may not occur, and that the description includes instances where said event or circumstance occurs and instances where it does not.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%.

A weight percent of a component, or weight %, or wt %, unless specifically stated to the contrary, is based on the total weight of the formulation or composition in which the component is included.

References in the specification and concluding claims to parts by weight of a particular element or component in a composition or product, denotes the weight relationship between the element or component and any other elements or components in the composition or product for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

As used herein, the term "substantially," in, for example, the context "substantially free of" refers to a composition having less than about 10% by weight, e.g., less than about 5%, less than about 1%, less than about 0.5%, less than about 0.1%, less than about 0.05%, or less than about 0.01% by weight of the stated material, based on the total weight of the composition.

It is further understood that the term "substantially," when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature, component, or a combination of the components. It is further understood that if the composition comprises more than one component, the two or more components can be present in any ratio predetermined by one of ordinary skill in the art.

The term "acidic cannabinoid" refers to a cannabinoid having one or more carboxylic acid functional groups. Examples of acidic cannabinoids include, but are not limited to, tetrahydrocannabinolic acid (THCA), cannabidiolic acid (CBDA), and cannabichromenic acid (CBC). Acidic cannabinoids are frequently the predominant cannabinoids found in raw (i.e., unprocessed) cannabis plant material.

As used herein, "cannabinoids" include, for example, phytocannabinoids found in Cannabis plants and other plants and synthetic cannabinoids. As used herein, "cannabinoid(s)" refers, for example and without limitation, to any of known form of cannabinoid and mixtures. Examples of cannabinoids include cannabigerol (CBG), cannabichromene (CBC), cannabidiol (CBD, CBDa and (−) trans-cannabidiol), cannabinol (CBN), tetrahydrocannabinol (THC), cannabicyclol (CBL), cannabielson (CBE), iso-tetrahydrocannabinol (iso-THC), cannabicitran (CBT), tetrahydrocannabivarin (THCV), decarboxylated tetrahydrocannabinol (THCa) and their derivatives, metabolites and another analogous, and combinations thereof, as well as the various strains. For example, and without limitation carbolic acid forms of cannabinoids, cannabinoid acids, cannabinoid salts, CBDa or THCa.

The term "cannabis" may encompass any combination of cannabis species, e.g., *Sativa*, *Indica*, and *Ruderalis*. It can be appreciated that cannabinoids can be contained in numerous other plants, including hops. The present invention can be applied to non-cannabis plants that contain cannabinoids.

As used herein, a "cannabis derived compound" refers to any compound which can be extracted from a cannabis plant material, such as a cannabinoid, a terpene, a flavonoid, and the like.

The term "cannabis oil" refers to a mixture of compounds obtained from the extraction of cannabis plants. Such compounds include, but are not limited to, cannabinoids, terpenes, terpenoids, and other compounds found in the cannabis plant. The exact composition of cannabis oil will depend on the strain of cannabis that is used for extraction, the efficiency and process of the extraction itself, and any additives that might be incorporated to alter the palatability or improve administration of the cannabis oil.

The term "CBD" refers to the cannabidiol molecule found in cannabis. It counteracts the psychoactive effects of THC resulting in less of a "high" in high-CBD cannabis than in low-CBD cannabis. It may be used interchangeably with CBDa.

The term "CBC" refers to the cannabichromene molecule found in cannabis. This molecule has been shown to have anti-depressant effects.

The term "CBG" refers to the cannabigerol molecule found in cannabis. This molecule is an antagonist to the CBI receptor and therefore a higher percentage creates less of the "high" effect in cannabis.

The term "CBN" refers to the cannabinol molecule found in cannabis. It has little to no psychoactive effect and generally exists in small amounts in cannabis plants.

The term "CBDV" refers to the cannabidivarin molecule found in cannabis. Similar to CBD, CBDV works as an antagonist to the CBI receptors in the brain.

The term "CBDa" refers to cannabidiolic acid in cannabis. CBDa can be converted into CBD when it is aged and heated.

A "lipid" is a molecule that is soluble in nonpolar solvents. Lipids include fats, fatty acids, and their derivatives, as well as sterol-containing metabolites such as cholesterols and waxes.

The term "mass ratio," as used herein, refers to the mass of one substance (S1) relative to the mass of another substance (S2), where both masses have identical units (e.g., grams), expressed as S1:S2. For a substance such as water with a density of about 1 mg/mL, it is understood that reference to a volume of water (e.g., in milliliters or mL) is equivalent to mass (e.g., in units of mg).

The term "THC" refers to the tetrahydrocannabinol molecule found in cannabis. It is often related to the psychoactive effects that are associated with cannabis. THC may refer to various types of THC, including 48 and 49. It may also be used interchangeably with THCa in the application.

The term "THCa" refers to the tetrahydrocannabinolic acid found in cannabis. THCa is found in living, raw plants and as the plant dries and/or is heated converts to THC.

As used herein, "trichome" refers to a fine outgrowth or appendage on plants and certain protists. They are of diverse structure and function. Examples are hairs, glandular hairs, scales, and papillae. In reference to cannabis, the trichome is a glandular trichome that occurs most abundantly on the floral calyxes and bracts of female plants.

A temperature or temperature range, as expressed herein, refers to the temperature or temperature range at a pressure of 1 atm and equivalents thereof. For example, the phrase "at a temperature equivalent to from about 210° F. to about 280° F. at a pressure of 1 atm" refers not only to the temperature range at the stated atmospheric pressure but also to equivalent temperatures at lower and higher atmospheric pressures. Thus, a stated temperature range can encompass a lower equivalent temperature range at a pressure lower than 1 atm and a higher equivalent temperature range at a pressure higher than 1 atm. Similarly, in some embodiments, a stated temperature range can encompass a higher equivalent temperature range at a pressure lower than 1 atm to a achieve a kinetic energy equivalent to that achieved at the stated temperature range.

Normally, cannabinoid extracts are intensely bitter, earthy, and unpleasant, owing respectively to the extracted cannabinoids, terpenes, flavonoids, and the complex interactions between them and other ingredients.

In another embodiment, the present invention includes a method of preparing an infused lipid composition that renders the normally unpleasant tasting concentrated cannabis oil flavorless or reduced in unpleasantness.

The present invention relates to methods of extraction and infusion of bioactive compounds from plant material into lipid compounds. In one embodiment, the present invention provides for methods of preparing lipid compositions infused with bioactive compounds from cannabis plant material. In one or more embodiments, the bioactive compounds from plant material comprise cannabinoids, cannabinoid acids, terpenes, terpenoids, and/or flavonoids and related compounds.

In one embodiment, the present invention provides for methods of preparing a bioactive compound-infused lipid composition and products made by such methods. In another embodiment, the present invention provides for methods of preparing a cannabis bioactive compound-infused lipid composition and products made by such methods. In one embodiment, the present invention provides for methods of preparing a cannabinoid-infused lipid composition and products made by such methods.

In some embodiments, the cannabinoid comprises 49 tetrahydrocannabinol (THC), cannabidiol (CBD), tetrahydrocannabinolic acid (THCA), cannabidiolic acid (CBDA), cannabigerolic acid (CBGA), cannabichromenenic acid (CBCA), cannabigerovarinic acid (CBGVA), tetrahydrocanabivarinic acid (THCVA), cannabidivarinic acid (CBDVA), cannabichromevarinic acid (CBCVA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethylether (CBGM), cannabielsoin (CBE), cannabicitran (CBT), or a combination thereof. In some embodiments, the cannabinoid comprises THC, THCA, CBD, CBDA or a combination thereof.

In some embodiments, the present invention provides for methods of producing an infused lipid composition comprising terpenes. In some embodiments, the infused lipid composition comprises terpenes and cannabinoids. In some embodiments, the infused lipid composition comprises terpenes, cannabinoids, and flavonoids.

Terpenes, sometimes referred to as terpenoids, are essential oil (EO) components present in numerous botanicals, and form the largest group of plant chemicals, with 15-20,000 terpenes that have been fully characterized (Langenheim J H. Higher plant terpenoids: A phytocentric overview of their ecological roles. J Chem Ecol. 1994 June; 20(6): 1223-80. doi: 10.1007/BF02059809).

Exemplary terpenes produced by Cannabis that can be extracted using the methods described herein comprise Limonene, Nerolidol, Phytol, Caryophyllene Oxide, Linalool, .alpha.-pinene, β-pinene, Eucalyptol, Trans-nerolido, Humulene, delta-3-carene, Camphene, Borneol, Valencene, Geraniol, Myrcene, Terpinolene, β-caryophyllene, selina-3 7(11)-diene, guaiol, 10-epi-y-Eudesmol, β-Eudesmol, α-Eudesmol, Bulnesol, α-Bisabolol, or a combination of any of these.

In some embodiments, the cannabinoid comprises a combination of THC and CBD. In some embodiments, the terpene comprises myrcene, terpinolene, β-caryophyllene, selina-3 7(11)-diene, guaiol, 10-epi-y-eudesmol, β-eudesmol, α-eudesmol, bulnesol, α-bisabolol or a combination thereof.

The person of ordinary skill will be able to select a Cannabis strain producing the desired terpene(s) for use with the extraction methods disclosed herein.

In some embodiments, the present invention provides for methods of producing an infused lipid composition comprising flavonoids. In some embodiments, the botanical extract comprises flavonoids and cannabinoids. In some embodiments, the botanical extract comprises flavonoids, terpenes, cannabinoids, or combinations thereof.

In Cannabis, at least 20 flavonoids have been identified, mainly belonging to flavone and flavonol subclasses. Exemplary flavonoids that can be extracted using the methods of the instant disclosure include, but are not limited to, cannflavin A, cannflavin B, cannflavin C, vitexin, isovitexin, apigenin, kaempferol, quercetin, luteolin, orientin or a combination of any of these. In one or more embodiments, the botanical extract comprises one or more flavonoids selected from the group consisting of cannflavin A, cannflavin B, cannflavin C, vitexin, isovitexin, apigenin, kaempferol, quercetin, luteolin, orientin or a combination thereof.

In another embodiment, the lipid compounds for infusion may include but are not limited to dairy butters, nut butters and plant oils. It can be appreciated that various other lipid sources can be used, and that particular lipid sources can be modified or processed to perform within the preferred temperature range requirements of the present invention. For example, cocoa butter/oil (also called theobroma oil), oil, canola oil, coconut oil, safflower oil, olive oil, sunflower oil, corn oil, soybean oil, ghee, and lard The method comprises (i) heating cannabis plant material for an appropriate time and temperature in order to substantially decarboxylate the cannabis plant material; (ii) extracting cannabinoids from the decarboxylated cannabis plant material by the use of solvents; and (iii) infusing lipid with the cannabinoids. In some embodiments, steps (a) and (b) may be repeated at least once.

Any part of the Cannabis plant may be used in the methods of the instant disclosure. For example, stems, leaves, seeds, flowers, or a combination thereof can be used as the starting material for the methods of the invention. In some respects, one or more parts of the plant are used in practicing the claimed methods. Alternatively, all parts of the plants may be used in practicing the claimed methods.

In one or more embodiments of the present invention, the method of preparing a botanical extract comprises (a) providing a cannabis plant material; (b) decarboxylation of the cannabis plant material by heating to convert cannabinoid acids present in the plant material to neutral (non-acid) cannabinoids (c) contacting an organic solvent with the decarboxylated cannabis plant material; (d) extracting at least one bioactive molecule from the decarboxylated cannabis plant material into the organic solvent, thereby producing an organic solvent comprising a botanical extract; (e) contacting the organic solvent comprising a botanical extract with a lipid compound; (f) infusing at least one bioactive molecule from the botanical extract material into the lipid compound, thereby producing a cannabinoid-infused lipid composition.

In another embodiment, the method of preparing a botanical extract comprises (a) providing a cannabis plant material; (b) decarboxylation of the cannabis plant material by heating the cannabis plant material to temperatures and for times which ensure at least 95% conversion of the acid cannabinoids from the acid form to their neutral form, while ensuring thermal degradation of THC to CBN is less than 10%; (c) contacting an organic solvent with the decarboxylated cannabis plant material; (d) extracting at least one bioactive molecule from the decarboxylated cannabis plant material into the organic solvent, thereby producing an organic solvent comprising a botanical extract; (e) contacting the organic solvent comprising a botanical extract with a lipid compound; (f) infusing at least one bioactive molecule from the botanical extract material into the lipid compound, thereby producing a cannabinoid-infused lipid composition; and (g) recovering the cannabinoid-infused lipid composition from the organic solvent; thereby producing an edible additive.

In another embodiment, the method of preparing a botanical extract comprises (a) providing a cannabis plant material; (b) decarboxylation of the cannabis plant material by heating the cannabis plant material to temperatures and for times which ensure (i) at least 90% conversion of the acid cannabinoids from the acid form to their neutral form, while ensuring thermal degradation of THC to CBN is less than 10% and (ii) and the cannabis plant material contains no more than 10% of moisture; (c) contacting an organic solvent with the decarboxylated cannabis plant material; (d) extracting at least one bioactive molecule from the decarboxylated cannabis plant material into the organic solvent, thereby producing an organic solvent comprising a botanical extract; (e) contacting the organic solvent comprising a botanical extract with a lipid compound; (f) infusing at least one bioactive molecule from the botanical extract material into the lipid compound, thereby producing a cannabinoid-infused lipid composition; and (g) recovering the cannabinoid-infused lipid composition from the organic solvent; thereby producing an edible additive.

In another embodiment, the methods further comprise the additional step of (x) filtering the organic solvent comprising a botanical extract; and (y) recovering the botanical extract from the organic solvent; thereby producing a botanical extract.

In some embodiments, the decarboxylation step is conducted at temperatures and for times which ensure at least 90, 91, 92, 93, 94, 95, 96, 97% or more conversion of the acid cannabinoids to their neutral (non-acid) form, while ensuring thermal degradation of THC to CBN is less than 10, 9, 8, 7, 6, 5% or less. THC and CBD are the neutral forms of THCA and CBDA.

In one or more embodiments, the present invention provides for a product created in accordance with the present methods with such an improved product having a reduced perceived sensation of the normally unpleasant taste or cannabis oil.

In one or more embodiments, the cannabinoid-infused lipid composition of the present invention can be used (i) directly as a medicine, natural health product, food product, or for recreational use, or (ii) as a raw material in the preparation of products, such as pharmaceutical, natural health products, food products, or recreational use products for known uses of decarboxylated cannabinoid(s).

Decarboxylation

The extraction and infusion of active components from plant materials begins with the decarboxylation of the cannabis material.

There are over 400 chemical compounds that define the chemical makeup of the cannabis plant. THC and CBD are the two most commonly identified compounds, and their symbiotic relationship gives the cannabis plant its many therapeutic properties.

Δ9-Tetrahydrocannabinol (THC), the main psychoactive component within the chemical makeup of the cannabis plant, is not readily available for consumption and absorption by a user, because in nature the THC exists as carboxylate acid, namely tetrahydrocannabinolic acid (THCA). THCA is not itself a psychoactive compound, however, studies have shown that it embodies properties such as anti-inflammation, anti-emetic, and neuroprotective aspects. Typically, removal of the carboxyl group is accomplished by a chemical reaction when heat is applied to the THCA, such as when cannabis plant material is smoked. This step is referred to as "decarboxylation" and it must be carried out at some point before or during the consumption of cannabis product in order for the THC to be available to the consumer.

Edible producers have the added task of decarboxylation of their cannabis material before or after infusing their products and sending them to market. Otherwise, the edible items, while still containing numerous beneficial cannabinoids, will not induce the intended psychoactive properties. The THCA must have already been converted to THC within the infused product, so that ingestion produces the desired effect.

The decarboxylation process can be accomplished in a variety of different ways and at any level of processing. Raw flower, bud or trim can be decarboxylated (without being smoked and before being processed down into concentrates) as can raw concentrates again, without being smoked or vaped and before being infused into edibles. In one or more embodiments, it is left to the edibles manufacturer at which point to decarboxylate their cannabis material, and this decision will be made on the basis of time, cost, availability, feasibility, and convenience.

The most effective tool for decarboxylation of cannabis is heat. Keeping the temperature relatively low helps prevent boiling off some of the other non-psychoactive yet highly beneficial cannabinoids in the cannabis material. For example, decarboxylating cannabis at a temperature of 240 degrees Fahrenheit for 60 minutes will convert most, if not all, of the THCA content into THC. However, in the process, the medicinally beneficial terpenoids and flavonoids with much lower evaporation points will have been boiled off, resulting in the loss of many of the believed and suspected health benefits from these compounds.

In one or more embodiments of the present invention, the cannabis plant material containing trichomes is first decarboxylated. In one embodiment, the plant material is decarboxylated by contacting cannabis plant material with heat at a temperature and for a time sufficient to decarboxylate the raw materials in preparation for infusion.

In another embodiment, the plant material is decarboxylated by the steps of:
  (a) heating the cannabis plant material to temperatures and for times which ensure:
    (i) at least 90% conversion of the acid cannabinoids from the acid form to their neutral form, while ensuring thermal degradation of THC to CBN is less than 10% and
    (ii) and the cannabis plant material contains no more than 10% of moisture;
  (b) recovering the cannabis plant material thereby producing decarboxylated cannabis plant material.

In some embodiments, the decarboxylation step is carried out prior to extraction with organic solvent and is conducted by heating the cannabis plant material to temperatures and for times which ensure at least 95% conversion of the acid cannabinoids from the acid form to their neutral (non-acid) form, while ensuring thermal degradation of THC to CBN is less than 10%.

In some embodiments, the decarboxylation step is conducted at temperatures and for times which ensure at least 90, 91, 92, 93, 94, 95, 96, 97% or more conversion of the acid cannabinoids to their neutral (non-acid) form, while ensuring thermal degradation of THC to CBN is less than 10, 9, 8, 7, 6, 5% or less.

Decarboxylation of cannabinoid acids is a function of time and temperature, thus at higher temperatures a shorter period of time will be taken for complete decarboxylation of a given amount of cannabinoid acid. In selecting appropriate conditions for decarboxylation consideration must, however, be given to minimizing thermal degradation of the desirable, pharmacological cannabinoids into undesirable degradation products, for example thermal degradation of THC to cannabinol (CBN).

In some embodiments, decarboxylation is carried out in a multi-step heating process in which the plant material is first heated to a first temperature for a first (relatively short) time period to evaporate off retained water and allow for uniform heating of the plant material; and second the temperature is increased to a second temperature for a second time period (typically longer than the first time period) until at least 95% conversion of the acid cannabinoids to their neutral form has occurred.

In some embodiments, the cannabis plant material is processed from *Cannabis sativa* or *Cannabis indica*. The cannabis plant material may or may not need to be pre-processed. For example, the raw cannabis plant material can be used directly for cannabis extraction. In some embodiments, the method further comprises grinding *Cannabis sativa* or *Cannabis indica* into ground cannabis plant material.

In some embodiments, the cannabis plant material is processed from *Cannabis sativa* or *Cannabis indica*. In some embodiments, the method further comprises grinding *Cannabis sativa* or *Cannabis indica* into ground cannabis plant material.

In one example, 10 ounces of trimmed cannabis flower or plant material may be gently broken up and placed on baking sheets. The flower is then placed in an oven and heated.

In one or more embodiments, the time of decarboxylation not to be less than 16 minutes and not more than 40 minutes. In one or more embodiments, the temperature of decarboxylation is not to be less than 180° F. and not more than 280° F. In another embodiment, thirty minutes at 250 degrees F. is enough to allow decarboxylation to take place with the flower.

In one or more embodiments, the temperature of decarboxylation is at least 150, 160, 170, 175, 180, 185, 190, 195° F. or more. In another embodiment, the temperature of decarboxylation is at most 295, 290, 285, 280, 275, 270, 265, 260, 255, 250, 245, 240° F. or less.

In one or more embodiments, the decarboxylation rates can be increased by narrowing the time and temp to not less than 200° F. and not more than 260° F., not more than 38 minutes or less than 21 minutes.

In one or more embodiments, the process results are improved when the cannabis product is decarboxylated between 220° F. and 240° F. at times not more than 30 minutes and not less than 26 minutes.

In one or more embodiments, the decarboxylation of the cannabis plant material is continued for a time of at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 120, 180, 240 minutes or more.

In one or more embodiments, the decarboxylation of the cannabis plant material is continued for a time of at most 240, 180, 120, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, minutes or fewer.

In one or more embodiments, the decarboxylation of the cannabis plant material is continued for a time in a range selected from the group consisting of 15-20, 20-25, 25-30, 30-45, 35-40, 15-45, 15-50, 10-55, 15-90, 15-120, 15-120, 10-125, 15-130, 15-180, 15-185, 220-225, 225-230, 230-235, 235-240 minutes.

In one or more embodiments, the decarboxylation of the cannabis plant material is continued until at least 60, 65, 70, 75, 80, 85, 90% or more of the cannabinoids are converted from THCa to THC within the plant material and the plant material contains 20, 19, 18, 17, 16, 15, 14, 13, 12, 11, 10% or less of moisture.

Using the following time and temp chart, calculate the decarboxylation time and temperature of the cannabis plant material input.

| | |
|---|---|
| 180° F. | 40 minutes |
| 190° F. | 38 minutes |
| 200° F. | 35 minutes |
| 210° F. | 33 minutes |
| 220° F. | 30 minutes |
| 230° F. | 28 minutes |
| 240° F. | 26 minutes |
| 250° F. | 23 minutes |
| 260° F. | 21 minutes |
| 270° F. | 18 minutes |
| 280° F. | 16 minutes |

In some embodiments, the cannabis plant material used may have a particle size from 0.2 microns to 1000 microns. This may be achieved by trimming the cannabis for trichrome materials. This may also be achieved by treating the cannabis for trichrome materials, lipid-based extracts, and/or synthesized fatty acids of a pharmaceutical composition using one or more of the following: alcohol, carbon dioxide, apple cider vinegar, water, freeze drying, ice water, or steam. The cannabis may be screened to remove residue or dregs using screens ranging from course (approximately 4000 microns) to fine (approximately 25 microns).

In one or more embodiments, the cannabis plant material plant may then be ball milled for 0.2 minutes to 6 hours until it has a particle size from 0.2 microns to 750 microns. In one or more embodiments, the average particle size is from 100 microns to 250 microns. The hybrid plant may also be cut, grated, blended, cooked, crunched, baked, compressed, pulverized, crushed, pressed, triturated, or grinded in order to achieve a particle size from 0.2 microns to 750 microns in size. The hybrid may also be converted to a gas or liquid as required for the targeted use. In one or more embodiments, the milled plant material is optionally coarsely milled. In some embodiments, the plant material is ground to provide a particle size between about 0.5 mm to about 5 mm. In one or more embodiments, the cannabis plant material plant is coarsely ground by mechanical means to achieve an average particle size of US Mesh 3.5-35. In another embodiment, the cannabis plant material plant is coarsely ground by mechanical means to achieve an average particle size of about 0.5 to about 10 mm. In another embodiment, the cannabis plant material plant is coarsely ground by mechanical means to achieve an average particle size of about 0.5 to about 4 mm.

In one embodiment, sonication can be used to loosen the cannabis plant material in contact with an appropriate solvent such as ethanol, and/or by breaking down cellular membranes making it suitable for extraction and/or decarboxylation. In another embodiment, maceration can be performed with a mortar and pestle to produce a cannabis plant material of a size and form suitable for extraction and/or decarboxylation.

All these actions may be performed on the hybrid plant before it is combined with other ingredients. All these actions may also be performed on the cannabis plant material after decarboxylation. Additionally, all these actions may be performed both before and after the cannabis plant material is combined with other ingredients.

In some embodiments, the step of decarboxylization of cannabis plant material is performed under atmospheric pressure. In one or more embodiments, the step of decarboxylization of cannabis plant material is performed at greater than atmospheric pressure. In another embodiment, the step of decarboxylization of cannabis plant material is performed at a pressure between 0-25 psi above atmospheric pressure. In another embodiment, the step of decarboxylization of cannabis plant material is performed at a pressure between 5-25 psi above atmospheric pressure. In another embodiment, the step of decarboxylization of cannabis plant material is performed at a pressure of at least 5, 10, 15, 20, 25 or more psi above atmospheric pressure.

In some embodiments, decarboxylation is carried out in a multi-step heating process in which the plant material is first heated to a first temperature for a first (relatively short) time period to evaporate off retained water and allow for uniform heating of the plant material; and second the temperature is increased to a second temperature for a second time period (typically longer than the first time period) until at least 95% conversion of the acid cannabinoids to their neutral form has occurred.

In some embodiments, the first step is conducted at a temperature in the range of 180° F. to 280° F. for 5-45 minutes. In some embodiments, the first temperature is about 180° F. and the first time period is about 10-25 minutes.

In some embodiments, the first step is conducted at a temperature in the range of 180° F. to 220° F. for 10-20 minutes. In some embodiments, the first temperature is about 180° F. and the first time period is about 15 minutes.

If the plant material is derived from cannabis plants having a high CBD content, the second temperature can be in the range from 180° F. to 280° F., for example about 260° F. and the second time period is in the range from 15 to 75 minutes, for example about 20 minutes. In some embodiments, the second temperature is in the range from 240° F. to 280° F., for example 260° F. and the second time period is in the range from 15 to 45 minutes, for example about 30 minutes.

If the plant material is derived from cannabis plants having a high THC content, the second temperature can be in the range from 180° F. to 240° F., for example about 230° F. and the second time period is in the range from 15 to 75 minutes, for example about 20 minutes. In some embodiments, the second temperature is in the range from 210° F. to 240° F., for example 220° F. and the second time period is in the range from 15 to 45 minutes, for example about 30 minutes.

Extraction

In one or more embodiments of the present invention, the extraction of trichomes from the decarboxylated cannabis plant material is by the use of solvents. In one embodiment, the decarboxylated cannabis plant material may be extracted in any non-aqueous solvent, including for example, ethyl alcohol, propyl alcohol, isopropyl alcohol, or butyl alcohol.

In one or more embodiments, the amount of solvent added to the decarboxylated cannabis plant material is sufficient such that the decarboxylated cannabis plant material is free flowing. The amount of solvent added to the decarboxylated cannabis plant material may be up to 95% v/v of the total volume of the solvent and decarboxylated cannabis plant material mixture. The amount of solvent added to the decarboxylated cannabis plant material is preferably up to 75% v/v. The amount of solvent added to the decarboxylated cannabis plant material is more preferably up to at least 40, 45, 50, 55, 60, 65% v/v or more.

Suitable alcohols for mixing with the decarboxylated cannabis plant material include alcohols that are suitable for food and/or natural products and/or pharmaceutical production. Examples of suitable alcohols are ethanol and isopropanol. The amount of alcohol added to the decarboxylated cannabis plant material is sufficient to make the decarboxylated cannabis plant material free flowing. The amount of alcohol added to the decarboxylated cannabis plant material may be up to 95% v/v, 90% v/v, 85% v/v, 80% v/v, 75% v/v, 70% v/v, 65% v/v, 60% v/v, 55% v/v, 50% v/v, or 45% v/v of the total volume of the alcohol and decarboxylated cannabis plant material mixture. The decarboxylated cannabis plant material may be mixed with an alcohol in a 1:15 w/v, 1:10 w/v, 1:5 w/v, 1:2 w/v ratio of extract to alcohol, and ranges there between.

In one embodiment, the solvent is an alcohol. In another embodiment, the alcohol is selected from ethanol and isopropanol. In another embodiment, the alcohol is ethanol.

In one or more embodiments, the solvent is an alcohol having a concentration no less than 5, 10, 15, 20, 25, 30, 35, 40, 45, 50, 55, 60, 65, 70% or more by volume and no more than 90, 85, 80, 75, 70, 65, 60, 55, 50, 45, 40, 35, 30, 25, 20, 15, 10, 5% or less by volume.

In one or more embodiments, the process results are increased as the percentage of alcohol increases. In one embodiment, the alcohol has a concentration of 10 to 50%. In another embodiment, the alcohol has a concentration of 15 to 50%. In another embodiment, the alcohol has a concentration of 15 to 20% when used with lipids that are predominantly saturated fatty acids.

In another embodiment, the alcohol has a concentration of 40 to 50% when used with lipids that are predominantly unsaturated fatty acids.

In one or more embodiments, the solvent is selected from the group consisting of: 80-100% ethanol (for example, 80%, 85%, 90%, 95%, 97%, 98%, 100%, and any integer or fraction of the integer thereof), ethylene glycol, isopropanol, or a combination of similar solvents.

In one or more embodiments, the extraction process described herein uses a ratio of 0.5-2 ounce by weight of plant material to 40-500 mL of solvent (carrier agent) in the mixture.

In another embodiment, the extraction process described herein uses a ratio of approximately 1 ounce by weight of plant material to 1000-2000 mL of solvent (carrier agent) in the mixture.

In another embodiment, the extraction process described herein uses a ratio of approximately 1 ounce by weight of plant material to at least 200, 300, 400, 500, boo, 700, Boo, 900, 1000, 1100, 1200 mL of solvent or more. In another embodiment, the extraction process described herein uses a ratio of approximately 1 ounce by weight of plant material to at most 4000, 3000, 2500, 2000 mL of solvent or less.

In one or more embodiments, the extraction is performed under ambient conditions in a temperature and humidity-controlled environment. In another embodiment, the following extraction chart is used to calculate the solvent extraction time by finding the cannabis plant material weight and the volume of solvent (e.g., alcohol):

|   | Plant Product Wt. | Volume of Solvent | Time (hrs) |
|---|---|---|---|
| i | 3.5 g | 62 cc | 48 hrs |
| ii | 3.5 g | 124 cc | 40 hrs |
| iii | 3.5 g | 188 cc | 32 hrs |
| iv | 3.5 g | 250 cc | 24 hrs |
| v | 3.5 g | 312 cc | 16 hrs |
| vi | 3.5 g | 375 cc | 8 hrs |

In one or more embodiments, the step of extraction of decarboxylated cannabis plant material is performed under ambient temperature and pressure. In another embodiment, the step of extraction of decarboxylated cannabis plant material is performed at a temperature from about −5° C. to 45° C. In another embodiment, the step of extraction of decarboxylated cannabis plant material is performed at a temperature from about 5° C. to 40° C. In another embodiment, the step of extraction of decarboxylated cannabis plant material is performed at a temperature from about 15° C. to 35° C. In another embodiment, the step of extraction of decarboxylated cannabis plant material is performed at a temperature from about 25° C. to 35° C.

In one or more embodiments, the solvent and the plant material are help at a temperature of about 15° C. to 35° C. for at least 1 hour prior to the step of extraction of decarboxylated cannabis plant material. In one or more embodiments, the solvent and the plant material are help at a temperature of about 25° C. to 35° C. for at least 2, 4, 6, 8, 10, 12 or more hours prior to the step of extraction of decarboxylated cannabis plant material.

In another embodiment, the time of extraction of decarboxylated cannabis plant material is for a time in the range of 1-48 hours, 2-24 hours, 2-18 hours, or 4-18 hours.

In one or more embodiments, the time of extraction not to be less than 30 minutes and not more than 48 hours. In another embodiment, the time of extraction of decarboxylated cannabis plant material is at least 1, 2, 4, 8, 12, 16, 20, 24, 30, 36, 42, 48 hours or more. In another embodiment, the time of extraction of decarboxylated cannabis plant material is at most 120, 60, 48, 42, 36, 30, 24, 20, 16, 12, 8 hours or less. In one or more embodiments, the extraction of the decarboxylated cannabis plant material is continued for a time of 4 hours to 48 hours. In other embodiments, the extraction of the decarboxylated cannabis plant material is continued for a time of 12 hours to 24 hours.

In one or more embodiments, after the extraction process is completed, the solvent, which now carries the extracted cannabinoids in solution, is collected.

In one or more embodiments, the collected extract solvent may be filtered by a cold filtration and/or centrifugation system. For example, a solid-liquid centrifuge can be used to separate extracted plant material from liquid solvent. Suitable solid-liquid filtration centrifuges to filter plant biomass from solvent will be known to the person of ordinary skill in the art.

In one or more embodiments, the output solvent may be returned to the reservoir container and recirculated to extraction chambers to increase the amount of cannabinoids, terpenes, and/or flavonoids. In some embodiments, the output solvent can be returned to the reservoir chamber and fresh plant material extracted at least 2, 3, 4, 5, 6, 7, 8, 9, 10 times or more.

In one or more embodiments, the solvent soaking time for amounts above 10 g is at least 6 hours and at most 48 hours. In one or more embodiments, the solvent soaking time for amounts above 10 g is at least 12 hours and at most 48 hours. In another embodiment, for amounts above log, add alcohol for the corresponding amount in the chart, e.g., for approximately 13 g (0.5 oz.), add 1½ cup (375 ml) of alcohol for extraction. In another embodiment, for 10 g and above during this portion of the process is in a maximum of 10 g increments for solvent, time will remain the same due to weight/volume of plant to solvent.

In one or more embodiments, the step of extraction of cannabis plant material is performed under atmospheric pressure. In one or more embodiments, the step of extraction of cannabis plant material is performed at greater than atmospheric pressure. In another embodiment, the step of extraction of cannabis plant material is performed at a pressure between 0-25 psi above atmospheric pressure. In another embodiment, the step of extraction of cannabis plant material is performed at a pressure between 5-25 psi above atmospheric pressure. In another embodiment, the step of extraction of cannabis plant material is performed at a pressure of at least 1, 2, 3, 4, 5, 10, 15, 20, 25 or more psi above atmospheric pressure.

In one embodiment of the extraction step, broken down cannabis plant material can be added to a solvent and concurrently sonicated. As used herein, sonication refers to the application of ultrasonic vibration (e.g., >20 kHz) to fragment cells, macromolecules, and membranes of the dried or undried cannabis plant material. Ultrasonic vibration can be provided by any means known in the art.

In one exemplary embodiment, sonication of a mixture of cannabis plant material and solvent can occur for 5-25 minutes at 25 C, where the ratio of cannabis plant material and solvent is such that all cannabis plant material is submerged in the solvent completely in the reaction vessel.

In one embodiment, upon the completion of extraction of the mixture of cannabis plant material and solvent, the solvent may be separated from the mixture. Removal of the solvent can occur by any means known in the art, including but not limited to filtration and/or evaporation. One embodiment for filtering after sonication is vacuum filtering over a glass sintered funnel to separate the resultant extract in the filtrate from the plant material. The latter can then be subjected to further extractions such as Soxhlet or other solvent extractions as is known to those skilled in the art, for example, SFE.

In one embodiment, extracted and decarboxylated cannabinoids are recovered by filtering the solvent from the extract of cannabis plant material to isolate the decarboxylated cannabinoids or decarboxylated cannabinoid comprising fraction.

In another embodiment, extracted and decarboxylated cannabinoids are recovered by filtering and/or activated carbon (e.g., charcoal) to obtain clarified solution for subsequent processing or use. Filtering agents can be washed with ethanol via vacuum filtration and extract can be dissolved in appropriate volume of suitable solvent such as ethanol and transferred to a funnel. A vacuum can then be applied and the filtering agent can be washed with the solvent until cannabinoids are completely eluted. The resulting filtrate can then be concentrated to dryness (e.g., at 25 C).

Separation can be by any suitable means such as a filtration, decanting, using a centrifuge or any combination of these. Filtering can include using any filter having any suitable mesh size (e.g., 4-400) or distribution of mesh sizes. Optionally, the filter can include as a cheese cloth, a sieve, a filter bag, a filter paper, or a strainer. Optionally one or more filter or filtering method can be used. In some implementations, the filtering includes a vacuum or pressurized filtration, a gravity filtration, or a centrifuge filtration.

In some implementations, a combination of times and ranges of temperatures can be used, providing, for example, temperature ramps (positive and negatives) held temperatures and combinations of these. In some implementations, one or more decarboxylation steps can be used, including different temperatures, temperature ramps, and using different ovens.

Infusion

In one or more embodiments of the present invention, the infusion of the extracted and decarboxylated cannabis plant material is by pressure infusion of cannabinoids, terpenes, and/or flavonoids into a lipid compound.

The lipid compound used may be any of a variety of oils or lipids that are suitable for human consumption, for smoking, or for application to human skin. The lipid compound may be any oil of animal, vegetable, or petrochemical origin. The lipid compound is substantially a nonpolar chemical substance that is hydrophobic and lipophilic but may include a low proportion (less than 10%) of non-oil components, which may be naturally occurring with the hydrophobic lipids or may be additives to it. The non-oil components may be, for example, proteins, waxes, alkaloids, or the like.

In one or more embodiments, the extracted and decarboxylated cannabis plant material-derived composition of this invention is mixed with an edible lipid compound. In another embodiment, the composition is mixed with an edible oil, e.g., include coconut oil, corn oil, olive oil, palm oil, cottonseed oil, peanut oil, rapeseed oil, safflower oil, sunflower oil, sesame oil, soybean oil, almond oil, pumpkin or squash seed oil, Brazil nut oil, cashew oil, hazelnut oil, macadamia nut oil, pecan oil, pine nut oil, pistachio oil, walnut oil, citrus oils, carob oil, cocoa butter, shea butter, hemp oil, flaxseed oil, grapeseed oil, other seed oils.

It can be appreciated that various lipid sources can be used, and that particular lipid sources can be modified or processed to perform within the preferred temperature range requirements of the present invention. In one method, cocoa butter oil, canola oil, coconut oil, safflower oil, olive oil, sunflower oil, corn oil, soybean oil, butter, ghee, and lard could be used.

In one embodiment, the lipid comprises a lipid or lipophilic vehicle comprising a liquid lipophilic vehicle, a semisolid lipophilic vehicle, or a mixture thereof. Suitable lipid or lipophilic vehicles include mineral oil; light mineral oil; natural oils (e.g., vegetable, corn, canola, sunflower, soybean, olive, coconut, cocoa, peanut, almond, cottonseed, persic, sesame, squalane, castor, cod liver, etc.) hydrogenated vegetable oil; partially hydrogenated oils; bee's wax (beeswax); polyethoxylated bee's wax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyldodecanol; myristyl alcohol; isopropyl myristate, isopropyl palmitate, stearic acid, stearyl alcohol, and others known in the art.

In another embodiment, the composition comprises a liquid lipophilic vehicle and a solid or semisolid lipophilic vehicle, such as a low melting hard lipid. In one embodiment, the liquid lipid or lipophilic vehicle can be sesame oil, olive oil, sunflower oil, canola oil, palmitoleic acid, oleic acid, myristoleic acid, linoleic acid, arachidonic acid, paraffin oil, mineral oil, or propylene glycol dicaprylate/dicaprate. In one aspect, the liquid lipid vehicle is sesame oil. In one aspect, the liquid lipid vehicle is or propylene glycol dicaprylate/dicaprate. In another embodiment, the composition comprises one or more low melting hard lipids such as polyethylene glycol glyceride esters, paraffin wax, or bee's wax.

In one or more embodiments, the extracted and decarboxylated cannabis plant material-derived composition of this invention is soaked in alcohol and lipid compound according to the steps:
(a) providing the extracted and decarboxylated cannabis plant material-derived composition based in a solvent solution;

(b) contacting extracted and decarboxylated cannabis plant material-derived composition based in a solvent solution with a lipid material;

(d) infusing at least one of cannabinoids, terpenes, and/or flavonoids into a lipid compound from the extracted and decarboxylated cannabis plant material-derived composition for a time and/or at a pressure and/or at a temperature sufficient to produce desired decarboxylated (biologically active) cannabinoid-infused lipid composition.

In another embodiment, the method of preparing a cannabinoid-infused lipid composition further comprises (e) recovering the cannabinoid-infused lipid composition from the organic solvent; thereby producing an edible additive.

In one or more embodiments, the step of infusion described herein is performed with the extracted and decarboxylated cannabis plant material-derived composition and the lipid material placed into a vessel or container creating a cannabis extract and lipid mixture. This cannabis extract and lipid mixture may be placed directly into the container.

In one or more embodiments, the step of infusion described herein is performed with the addition of water to the extracted and decarboxylated cannabis plant material-derived composition and the lipid material placed into a vessel or container creating a cannabis extract, lipid, and water mixture or dispersion.

In one embodiment, the mixture or dispersion comprises a final concentration of less than 30% alcohol by volume. In another embodiment, the mixture or dispersion comprises a final concentration of less than 30, 25, 20, 15, 10% or less alcohol by volume. In another embodiment, the mixture or dispersion comprises a final concentration of 10-25% alcohol by volume. In another embodiment, the mixture or dispersion comprises a final concentration of 15-20% alcohol by volume. In another embodiment, the mixture or dispersion comprises a final concentration less than about 10%, less than about 5%, less than about 1%, less than about 0.5%, less than about 0.1%, less than about 0.05%, or less than about 0.01% of alcohol by volume.

In one embodiment, the final concentration of the mixture is maintained at less than about 20% alcohol by volume in order to reduce degradation of lipids. In one embodiment, water is added to reduce the final concentration of the mixture to less than about 20% alcohol by volume whenever the mixture comprises a substantial amount of animal-derived lipid material for infusion. In another embodiment, water is added to reduce the final concentration of the mixture to less than about 20% alcohol by volume whenever the mixture comprises a substantial amount of lipid that will remain solid at room temperature. In another embodiment, water is added to reduce the final concentration of the mixture to less than about 20% alcohol by volume whenever the mixture comprises a substantial amount of saturated fatty acids for infusion.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the 9th and loth carbon atom as for palmitoleic acid (16:1) and oleic acid (18:1)), while "polyunsaturated fatty acids" (or "PUFAs") have at least two double bonds along the carbon backbone (e.g., between the 9th and loth, and 12th and 13th carbon atoms for linoleic acid (18:2); and between the 9th and loth, 12th and 13th, and 15th and 16th for [alpha]-linolenic acid (18:3)). PUFAs can be classified into two major families (depending on the position (n) of the first double bond nearest the methyl end of the fatty acid carbon chain). A "saturated fatty acid" or "SFA" is a type of fat in which the fatty acid chains have all, or predominantly all, single bonds.

In some embodiments, the lipid material comprises polyunsaturated fatty acids (PUFA). In some embodiments, the lipid material comprises saturated fatty acids (SFA). In some embodiments, the lipid material comprises PUFA and SFA. As used herein, the PUFA/SFA index refers to the ratio of PUFA to SFA in the lipid material. In some embodiments, the lipid material comprises a PUFA/SFA index of at least 7, at least 8, at least 9, at least 10, at least 20, at least 30, at least 40, at least 50, at least 60, at least 70, at least 80, at least 90, at least 100, at least 110, at least 120, at least 130, at least 140 or at least 150. In another embodiment, water is added to reduce the final concentration of the mixture to less than about 20% alcohol by volume whenever the lipid material comprises a PUFA/SFA index of less than 10, 9, 8, 7, 6, 5 or less.

In one embodiment, the container is a pressurizable container suitable for being pressurized at least up to 50 psi and preferably up to 80, 90, 100 psi or more. In another aspect, the pressurizable container can be pressurized to a higher pressure.

In another aspect of the invention, the pressurizable container has an interior large enough to receive the amount of cannabis extract and lipid mixture being processed and can be closed and/or sealed, such as with a lid or door. An air compressor or other pressure inducing mechanism may be attached to an inlet to increase the pressure within the container (after closure) to the desired pressure.

After sealing the pressurizable container, it is pressurized to a desired level of pressure. In one embodiment, the specific pressure is in the range of 1 to 500 psi. In another embodiment, the specific pressure is in the range of 1 to 100 psi. In another embodiment, the pressure is in the range between 1-25 psi. Additionally, the container (containing the cannabis extract and lipid mixture) is heated to a specific temperature in the range of 90 to 190 degrees Fahrenheit, and preferably in the range of 125 to 175 degrees Fahrenheit. The heat may be generated by an integrated energy source or an external energy source. The energy source provides thermal energy in a form such as by radiant heat, heated air or other fluid, electromagnetic heat induction, electric current, and any combination thereof.

The cannabis extract and lipid mixture remains in the sealed, heated, pressurized container for a development period of time during which the cannabinoids, terpenes, and/or flavonoids are infused from the cannabis extract into the lipid material.

The infusion time is in the range of 30 minutes to 48 hours. In one embodiment, the infusion time is in the range from one to thirty hours. In one embodiment, the infusion time is from one to four hours. The infusion time may be based on factors such as the type of cannabis extract and lipid mixture, the specific temperature deemed optimum for the particular type of cannabis extract and lipid mixture, the pressure selected as optimum for the particular type of cannabis extract, the type of alcohol, the type of lipid, the type and amount of any additive, the ratio of lipid to alcohol, the ratio of the weight lipid/alcohol mixture to the weight of the cannabis extract and lipid mixture, and the like.

After waiting the specific infusion time, the lipid/solvent mixture may be removed from the container such as by a pump.

In one or more embodiments, after the infusion process is completed, the lipid/solvent mixture, the process further comprises separating a lipid containing fraction from the solvent fraction. The separation can be by any useful method, for example by vacuum filtration, decanting, centrifuge, or a combination of these. As referred to herein, the lipid containing fraction can include other materials, such as waxes, fats, and lipids.

In one or more embodiments, after the infusion process is completed, the lipid/solvent mixture, which now carries the cannabinoids and terpenes, is drained into a cold filtration/centrifugation system. Suitable solid-liquid filtration centrifuges to filter plant biomass from solvent will be known to the person of ordinary skill in the art.

In some embodiments, the methods of preparing a Cannabis extract described herein comprise winterization and/or de-waxing. Winterization and de-waxing are methods to remove undesired Cannabis lipids and waxes from Cannabis extracts. Winterization can be achieved by dissolving a non-polar substance (e.g., the cannabinoid extract) into a polar solvent (e.g., ethanol) at sub-zero temperatures. This separates waxes and lipids from the cannabinoid extract, forcing them to collect at the top of the mixture for easy filtration.

An exemplary winterization method is described in U.S. Pat. No. 7,344,736. Ethanol is added to the Cannabis extract in the ratio of 2:1 ethanol volume to weight. The ethanolic solution is then cooled to −20° C.+/−5° C. and held at this temperature for approximately 48 hours. On completion of the winterization, the precipitated waxes and lipids are removed by cold filtration through a 20 μm filter.

De-waxing also uses low temperatures to separate waxes and lipids from Cannabis extract. In de-waxing, Cannabis extract mixed with a solvent such as butane is cooled to low temperatures (e.g., −20° C. or below) which makes the waxes and lipids insoluble in the butane solution. Once the waxes and undesired lipids have separated from the solvent, the mixture is passed through a variety of micron screens, effectively filtering out all undesired waxes and lipids. An exemplary de-waxing protocol comprises chilling the Cannabis extract and butane composition to low temperatures, then running the composition through a Buchner funnel that is attached to a passive vacuum, thus filtering out waxes and lips and producing a pure final product. The filtered product is then passed to a heated chamber where the butane can be removed through evaporation.

In one embodiment, a portion of the alcohol may be removed from the lipid/alcohol mixture in order to leave a cannabinoid-infused lipid product substantially-free of alcohol.

In one or more embodiments, all or part of the alcohol may be removed from the lipid/alcohol mixture in order to leave a cannabinoid-infused lipid product. In one embodiment, French presses, press style machines, or centrifuge processes can be utilized in order to draw off the cannabinoid-infused lipid product after separation from the solvent.

The newly created cannabinoid-infused lipid product is then removed from the container and is ready for packaging for sale or for use.

Storage

In some embodiments, the herein described procedures afford a cannabis-infused product which incorporates the cannabinoid profile in a stable manner. In other words, the cannabis-infused product advantageously remains stable in that there is close to no deterioration of the product appearance within the expected storage shelf-life. In some embodiments, a cannabis-infused product provided herein may be stable for at least about 1, 2, 3, 4, 5, 6 months or more at 4° C. In some embodiments, a cannabis-infused product provided herein may be stable for at least about 1, 2, 3, 4, 5, 6 months or more at room temperature.

In one or more embodiments, once the cannabis-infused lipid product has been recovered, the cannabis-infused lipid product can be stored in a cool, dark, and dry environment until further use. In one aspect, for example, the cannabis-infused lipid product can be stored at a temperature equivalent to about 25° C. or less at a pressure of 1 atm (i.e., room temperature or below).

As used herein, "shelf life" refers to a time period within which the provided compositions retain desirable organoleptic properties, for example, the ability of the provided compositions to retain desirable organoleptic properties for a period of time, for example, for at least or more than 1, 2, 3, 4, or more weeks, typically at least or more than 1, 2, 3, 4, 5, 6, 7, 8, 9, 10, 11, 12, or more months, or at least or more than 1, 2, 3, 4, or more years. In one example, the compositions retain desirable organoleptic properties if they exhibit one or more of these described characteristics, over time, when kept at a particular temperature. In one example, the compositions retain desirable organoleptic properties at room temperature, for example, 25° C. or about 25° C. In another example, the compositions retain desirable organoleptic properties at between 19° C. and 25° C. In another example, the compositions retain desirable organoleptic properties at refrigerated temperatures, for example, 4° C. or about 4° C., or at frozen temperatures, for example, at −20° C. or about −20° C. In another example, the compositions retain desirable organoleptic properties at elevated temperatures, for example, at 40° C. or at about 40° C.

As used herein, "room temperature" and "ambient temperature" are used to describe a temperature that is common in one or more enclosed spaces in which human beings typically are or reside. Room temperature can vary, but generally refers to temperatures between or between about 19° C. and 25° C. with an average of 23° C. When a composition is stored at room temperature, it should be understood it is generally kept at a temperature within this range or about within this range.

As used herein, "refrigerated temperature" refers to a temperature that is common in a refrigerator, for example, a household or restaurant refrigerator, for example, a temperature that is cooler than room temperature, but typically a few degrees above the freezing point of water. Typically, refrigerated temperatures are between or between about 0° C. and 10° C., for example, at or about 4° C. When a composition is stored at a refrigerated temperature, it should be understood that it is kept at a temperature common to household or industrial refrigerators.

As used herein, the stability of a composition provided herein refers to the length of time at a given temperature the emulsion is stable, and/or that greater than 10%, 20%, 30%, 40%, 50%, 60%, 70%, 80%, 85%, 90%, 91%, 92%, 93%, 94%, 95%, 96%, 97%, 98% or 99% of the initial amount of the agent to be delivered, e.g., cannabidiol (CBD) and/or THC, is present in the composition. Thus, for example, a composition that is stable for 30 days at 25° C. would have greater than 10%, 20%, 30%, 40%, 50%, 60%, 70%, 80%, 85%, 90% 91%, 92%, 93%, 94%, 95%, 96%, 97%, 98% or 99% of the initial amount of active ingredient present in the composition at 30 days following storage at 25° C.

In some embodiments, the CBD concentration in the composition remains consistent (a loss of less than or equal to about: 0.5%, 1%, 2%, 3%, 5%, or ranges including and/or spanning the aforementioned values) for a period of at least about 30 days, 60 days, 90 days, or 120 days when stored at room temperature, refrigeration, and up to 40° C. In some embodiments, when stored at room temperature, refrigeration, and up to 40° C., the composition is stable (e.g., the particle size or CBD concentration in the nanoparticles remains consistent and/or has a change of less than or equal to about: 0.5%, 1%, 2%, 5%, or ranges including and/or spanning the aforementioned values) for a period of at least about: 2 weeks, 30 days, 2 months, 3 months, 6 months, 9 months, 1 year, or ranges including and/or spanning the aforementioned measures of time.

In one embodiment, one or more additives may be added to, and incorporated into, the cannabis extract and lipid mixture before, during or after the mixture is created. This allows the additive to be mixed with the cannabis extract and lipid and to be incorporated into the cannabis extract and lipid mixture. The additive is then additionally infused into the lipid.

In one embodiment, the additive may be any of a variety of ingredients that augment or complement the lipid and/or the cannabis extract and lipid mixture and/or that augments or complements the health benefits of the cannabinoid-infused lipid product.

In addition to improving therapeutic benefits, the additive may improve the look or presentation, the taste or flavor, the smell, the mouth feel, the ease of application, the ability to smoke a smokable end-product, or another characteristic of the cannabinoid-infused lipid product. The additive may be all natural, all artificial, or a blend of natural and artificial components. In one aspect of the invention, the additive is a flavor enhancing material may be used, such as a fruit flavoring (apple, strawberry, peach, grape, lemon, etc.), a nut flavoring, an herbal scent and/or flavoring (mint, lavender, rosemary, eucalyptus, etc.), or the like. In another aspect, the additive may be a vitamin or vitamin mixture. In an additional aspect the additive may be a nutraceutical or other health-benefiting additive. In a further aspect, the additive may be terpenes, cannabinoids, or entourage chemicals from the Cannabis plant. In yet another aspect, the additive may be nicotine, which may provide benefits to the user including aiding in smoking cessation, improvement in brain function, combating depression, increasing attention, and preventing Parkinson's disease.

In one or more embodiments, the infusion process described herein uses a ratio of about 0.5-2 grams by weight of the extracted and decarboxylated cannabis plant material-derived composition to about 10-500 grams of lipid material.

In another embodiment, the extraction process described herein uses a ratio of approximately 1 gram by weight of the extracted and decarboxylated cannabis plant material-derived composition to about 20-200 grams of lipid material.

In another embodiment, the extraction process described herein uses a ratio of approximately 1 gram by weight of the extracted and decarboxylated cannabis plant material-derived composition to at least 10, 20, 25, 30, 35, 40, 45, 50, 55, 60 grams or more of lipid material.

In another embodiment, the extraction process described herein uses a ratio of approximately 1 gram by weight of the extracted and decarboxylated cannabis plant material-derived composition to at most 500, 450, 400, 350, 300, 250, 200, 150, 100 grams of lipid material.

In another embodiment, the extraction process described comprises the steps:
a) 64 grams of lipid compound is mixed per 1 gram cannabis material to be infused into a pressure vessel;
b) Add 1 cup of water to the pressure vessel and add 1 cup for each additional 4 g of cannabis material placed in the pressure vessel;
c) Wherein the lipid compounds for infusion may include but are not limited to dairy butters, nut butters, and plant oils;
d) Using the following pressure infusion chart, calculate the pressure, temperature, and time to run the pressure vessel;
  i. Time of infusion is not to be less than 1 hour and not to exceed 4 hours;
  ii. Pressure in the vessel is not to be less than 3 psi and not more than 15 psi;
  iii. Temperature of the vessel is not to be less than 221° F. and not more than 250° F.;
  iv.

CHART

| Pressure (psi) | Temperature (° F.) | Time (hrs) |
|---|---|---|
| 3 psi | 221° F. | 4 hrs |
| 4 psi | 225° F. | 3 hrs 40 min. |
| 6 psi | 229° F. | 3 hrs 20 min. |
| 7 psi | 233° F. | 3 hrs |
| 9 psi | 237° F. | 2 hrs 40 min. |
| 10 psi | 239° F. | 2 hrs 20 min. |
| 12 psi | 243° F. | 2 hrs |
| 13 psi | 246° F. | 1 hr 40 min. |
| 14 psi | 249° F. | 1 hr 20 min. |
| 15 psi | 250° F. | 1 hr |

In one or more embodiments, the infusion can be obtained between 3-6 psi and 4 hrs-3 hrs 20 min. In one or more embodiments, the infusion can be increased between 7-10 psi and 3 hrs-2 hrs 20 min. In one or more embodiments, the peak infusion was obtained between 12-15 psi and 2 hrs and 1 hr.

In some embodiments, the step of lipid infusion of the extracted and decarboxylated cannabis plant material-derived composition is performed under atmospheric pressure. In one or more embodiments, the step of lipid infusion of the extracted and decarboxylated cannabis plant material-derived composition is performed at greater than atmospheric pressure.

In one or more embodiments, the pressure during infusion comprises a pressure level between 1 to 100 psi. In another embodiment, the step of lipid infusion of the extracted and decarboxylated cannabis plant material-derived composition is performed at a pressure between 0-25 psi above atmospheric pressure. In another embodiment, the step of lipid infusion of the extracted and decarboxylated cannabis plant material-derived composition is performed at a pressure between 2-25 psi above atmospheric pressure. In another embodiment, the step of lipid infusion of the extracted and decarboxylated cannabis plant material-derived composition is performed at a pressure of at least 1, 2, 3, 4, 5, 10, 15, 20, 25 or more psi above atmospheric pressure. In another embodiment, the step of lipid infusion of the extracted and decarboxylated cannabis plant material-derived composition is performed at a pressure of at least 2, 2.5, 2.6, 2.7, 2.8, 2.9, 3, 3.1, 3.2, 3.3, 3.4, 3.5 or more psi above atmospheric pressure. In another embodiment, the step of lipid infusion of the extracted and decarboxylated cannabis plant material-derived composition is performed at a pressure of at most 20, 19, 18, 17, 16, 15, 14, 13, 12, 11, 10, 9, 8, 7, 6, 5 psi or less above atmospheric pressure.

In one or more embodiments, the time of lipid infusion is not to be less than 30 minutes and not more than 24 hours.

In one or more embodiments, the temperature of lipid infusion is not to be less than 180° F. and not more than 280° F. In another embodiment, 1-4 hours at 220-260 degrees is enough to allow lipid infusion to take place.

In one or more embodiments, the temperature of lipid infusion is at least 190, 195, 200, 210, 220° F. or more. In another embodiment, the temperature of decarboxylation is at most 280, 275, 270, 265, 260, 255, 250, 245, 240, 235, 230, 225° F. or less.

In one or more embodiments, the lipid infusion rates can be increased by narrowing the time and temp to not less than 200° F. and not more than 260° F., not more than 8 hours and not less than 30 minutes.

In one or more embodiments, the process results are improved when the lipid infusion is performed between 220° F. and 250° F. at times not more than 4 hours and not less than 1 hour.

In one or more embodiments, after the infusion process is completed, the edible cannabinoid-infused lipid composition is collected.

In one or more embodiments, after the infusion process is completed, the edible cannabinoid-infused lipid composition is generated without excessive decarboxylation and infusion generated heavy organics, which carry over unpleasant flavors. In one or more embodiments, the edible cannabinoid-infused lipid composition is generated with a darker color due to increased amount of nondegraded chlorophyll. In some embodiments, the additional nondegraded chlorophyll present provides for a flavor that is much lighter or non-existent that methods that provide for degradation of the chlorophyll into heavy organics.

Food Products

The present invention also provides for a cannabinoid-infused lipid composition that is edible, which is made by the methods disclosed herein. In another embodiment, the cannabinoid-infused lipid composition does not have a disagreeable taste. In another embodiment, the cannabinoid-infused lipid composition is used in the preparation of other products.

In one or more embodiments, the cannabinoid-infused lipid composition of the present invention can be used (i) directly as a medicine, natural health product, food product, or for recreational use, or (ii) as a raw material in the preparation of products, such as pharmaceutical, natural health products, food products, or recreational use products for known uses of decarboxylated cannabinoid(s).

Another aspect of the invention is a food product comprising a cannabinoid-infused lipid composition or synthetic cannabinoid-derived composition of this invention such that the food comprises at least one cannabinoid. In one embodiment, the food product is a food product or a confection. Examples of a food products include, e.g., cake, muffin, brownie, cookie, cracker, doughnut, or biscuit. Examples of a confection include e.g., caramel, chocolate, nougat, chewing gum, toffee, lozenge, fondant, halvah, jelly, gelatin, candies, e.g., gummies (e.g., gummy bears), suckers or lollipops, licorice, marshmallow, taffy, or marzipan. In another embodiment, the food product is a non-farinaceous food product. Examples of other food product include e.g., a dairy product, a meat product, a fruit product, or a vegetable product. Preferred examples of a drinkable food product include beverages, such as tea, herbal tea, coffee, juice, bottled water, carbonated beverages, smoothies, sports, or other rehydration drinks, mocktails or alcoholic beverages.

In another embodiment, the food product is a cannabinoid-containing edible. Edibles come in many forms and can be any product that is suitable, e.g., non-toxic, for placing into the mouth of a human, whether ingested, absorbed, or only chewed or sucked on and at least a portion discarded, etc. Illustrative examples of human edible products include chewing or bubble gums, mints, suckers, jawbreakers, lozenges, hard candies, gummy candies, taffies, chocolates, baked goods such as muffins, brownies, cookies, crackers, granola or meal replacement bars, smokeless inhalation powders, honey, syrup, spreads, and dissolving strips. For example, a chewing-gum may have a hard shell. The person of skill will readily understand how to infuse a product base to obtain the herein described cannabis-infused product.

For example, in order to infuse a chewing gum base, the person of skill may proceed to contact and mix the chewing gum ingredients (such as gum base [e.g., elastomers, waxes, and resin], sweeteners, glycerin, plasticizer and colors) with an embodiment of the herein described precursor composition and process the mixture to obtain the cannabis-infused chewing gum.

For example, the person of skill may mix an embodiment of the herein described cannabinoid-infused lipid composition including 0.69 wt. % THC with a chewing gum base (product base) including: 75.5 wt. % gum base, xylitol 14 wt. %, glycerin 4.5 wt. %, saccharine 0.38 wt. %, peppermint aroma oil 1.5 wt. %, peppermint powder 1.5 wt. %, and water 2.3 wt. % in order to obtain a 10 mg THC gum.

In another embodiment, the cannabinoid-infused lipid composition is used in liquid products, which can be used in many liquid applications. For example, such cannabis-infused liquid composition can be used for ingestion or application to a user's skin or mucous membrane.

The liquid compositions may come in many forms—including but without being limited to beverages, gels, creams, custard, pudding, honey, syrup, broth, soup, gelatin, yogurt, puree, jelly, sauce, liquid eggs, or salad dressing.

In some embodiments, the cannabis-infused lipid composition provided herein can be an edible or liquid contained in a packaging unit, the unit comprising less than 1000 mg, or less than 900 mg, or less than Boo mg, or less than 700 mg, or less than 600 mg, or less than 500 mg, or less than 400 mg, or less than 300 mg, or less than 200 mg, or less than 100 mg, or less than 50 mg, or less than 40 mg, or less than 30 mg, or less than 20 mg, or less than 10 mg, or less than 5 mg, or less than 2.5 mg of a specific cannabis extract such as THC, CBD, terpene (e.g., D-limonene) or any mixtures thereof. In some embodiments, the beverage may include, for example, per packaging unit up to 1 g, up to 750 mg, up to 700 mg, up to 650 mg, up to 600 mg, up to 550 mg, up to 500 mg, up to 450 mg, up to 400 mg, up to 350 mg, up to 300 mg, up to 250 mg, up to 200 mg, up to 150 mg, up to 100 mg, up to 50 mg, up to 40 mg, up to 35 mg, up to 30 mg, up to 25 mg, up to 20 mg, up to 15 mg, up to 10 mg, up to 9 mg, up to 8 mg, up to 7 mg, up to 6 mg, up to 5 mg, up to 4 mg, up to 3 mg, up to 2 mg, or up to 1 mg of a specific cannabis extract such as THC, CBD, terpene (e.g., D-limonene) or any mixtures thereof, and the like.

Compositions for Cannabis Extracts

In another aspect of this disclosure, also provided is a composition comprising the cannabinoid-infused lipid composition prepared by the method and system as described above. In one embodiment, the composition further comprises an additive, a pharmaceutical acceptable carrier, or an adjuvant to the cannabis component.

The composition can be an oral dosage composition, a pulmonary or nasal dosage composition, or a topical dosage composition. The compositions can be in the form of a solution, a spray, or a powder. In some embodiments, the composition is in the form of a tablet, a capsule, a jelly, a cream, an ointment, a suspension, a spray, or a chewing gum.

Pharmaceutical compositions or medicaments can be formulated by standard techniques or methods well-known in the art of pharmacy using one or more physiologically acceptable carriers or excipients. Suitable pharmaceutical carriers are described herein and in, e.g., "Remington's Pharmaceutical Sciences" by E. W. Martin. Cannabis oil extracts can be formulated for administration by any suitable route, including, but not limited to, orally, topically, nasally, rectally, vaginally, pulmonary, parenterally (e.g., intravenously, subcutaneously, intramuscularly, etc.), and combinations thereof. In some embodiments, the cannabis oil is diluted in a liquid, e.g., a carrier oil. The most suitable route of administration in any given case will depend in part on the condition being treated as well as the response of the subject to the particular route of treatment.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, maltodextrin, lecithin, agarose, xanthan gum, guar gum, sorbitol, cellulose (e.g., ethyl cellulose, microcrystalline cellulose), glycine, pectin, polyacrylates and/or calcium hydrogen phosphate, calcium sulfate, (b) lubricants; e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium or potassium salt, or effervescent mixtures; (e) wetting agents, e.g., sodium lauryl sulfate, and/or (f) absorbents, colorants, flavors, and sweeteners. Tablets can be either uncoated or coated according to methods known in the art. The excipients described herein can also be used for preparation of buccal dosage forms and sublingual dosage forms (e.g., films and lozenges) as described, for example, in U.S. Pat. Nos. 5,981,552 and 8,475,832. Formulation in chewing gums as described, for example, in U.S. Pat. No. 8,722,022, is also contemplated.

Further preparations for oral administration can take the form of, for example, solutions, syrups, suspensions, and toothpastes. Liquid preparations for oral administration can be prepared by conventional means with pharmaceutically acceptable additives, for example, suspending agents, for example, sorbitol syrup, cellulose derivatives, or hydrogenated edible fats; emulsifying agents, for example, lecithin, xanthan gum, or acacia; non-aqueous vehicles, for example, almond oil, sesame oil, hemp seed oil, fish oil, oily esters, ethyl alcohol, or fractionated vegetable oils; and preservatives, for example, methyl or propyl-p-hydroxybenzoate or sorbic acid. The preparations can also contain buffer salts, flavoring, coloring, and/or sweetening agents as appropriate.

Typical formulations for topical administration include creams, ointments, sprays, lotions, hydrocolloid dressings, and patches, as well as eye drops, ear drops, and deodorants. Cannabis oils can be administered via transdermal patches as described, for example, in U.S. Pat. Appl. Pub. No. 2015/0126595 and U.S. Pat. No. 8,449,908. Formulation for rectal or vaginal administration is also contemplated. The cannabis oils can be formulated, for example, using suppositories containing conventional suppository bases such as cocoa butter and other glycerides as described in U.S. Pat. Nos. 5,508,037 and 4,933,363. Compositions can contain other solidifying agents such as shea butter, beeswax, kokum butter, mango butter, illipe butter, tamanu butter, carnauba wax, emulsifying wax, soy wax, castor wax, rice bran wax, and candelilla wax. Compositions can further include clays (e.g., Bentonite, French green clays, Fuller's earth, Rhassoul clay, white kaolin clay) and salts (e.g., sea salt, Himalayan pink salt, and magnesium salts such as Epsom salt).

The compositions set forth herein can be formulated for parenteral administration by injection, for example, by bolus injection or continuous infusion. Formulations for injection can be presented in unit dosage form, for example, in ampoules or in multi-dose containers, optionally with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure, buffers, and/or other ingredients. Alternatively, the compositions can be in powder form for reconstitution with a suitable vehicle, for example, a carrier oil, before use. In addition, the compositions may also contain other therapeutic agents or substances.

The compositions can be prepared according to conventional mixing, granulating, and/or coating methods, and contain from about 0.1 to about 75%, preferably from about 1 to about 50%, of the cannabinoid-infused lipid composition. In general, subjects receiving a cannabinoid-infused lipid composition orally are administered doses ranging from about 1 to about 2000 mg of cannabis oil. A small dose ranging from about 1 to about 20 mg can typically be administered orally when treatment is initiated, and the dose can be increased (e.g., doubled) over a period of days or weeks until the maximum dose is reached.

In some embodiments, the composition is an oral dosage composition, a pulmonary or nasal dosage composition, or a topical dosage composition. The composition may be in the form of a solution, a spray, or a powder, a tablet, a capsule, a jelly, a cream, an ointment, a suspension, a spray, or a chewing gum.

Also within the scope of this disclosure is a unit dose of the composition as described above. In some embodiments, the unit dose comprises an amount of the composition selected from the group consisting of: trace amount, 0.01-0.05 mg, 0.05-0.1 mg, 0.1-0.5 mg, 0.25-1 mg, 0.5-15 mg, 0.5-2.5 mg, 1.0-2.5 mg, 2.5-5 mg, 5.0-7.5 mg, 5.0-10 mg, 1.0-25 mg, 25-50 mg, 50-75 mg, 75-100 mg, 10-20 mg, 10-15 mg, and 15-20 mg, 20-30 mg, 30-40 mg, 40-50 mg, 50-60 mg, 60-70 mg, 70-80 mg, 80-90 mg, 90-100 mg, 1-100 mg, 100-125 mg, 125-150 mg, 150-175 mg, 175-200 mg, and >200 mg.

In some embodiments, the composition may further comprise a second agent selected from the group consisting of: cannabinoids, terpenes, anti-insomnia, anti-tussive, opioid analgesic, decongestant, non-opioid analgesic/anti-inflammatory drug, anti-migraine drug, anti-emetic, anti-histamine, proton pump inhibitor, $H_2$ antagonist/$H_2$ blocker, tranquilizer, anticonvulsant, hypnotic, muscle relaxant, antipsychotic, anti-diarrheal, Attention Deficit and Hyperactivity Disorder (ADHD) drug, anti-Parkinson disease drug, benzodiazepine, benzodiazepine antagonist, barbiturate, barbiturate antagonist, stimulant, stimulant antagonist, antidepressant, nutraceutical, nicotine, BCS Class II active ingredient, BCS Class IV active ingredient, an anti-multiple sclerosis (MS) drug, ethyl pyruvate, melatonin, caffeine, resveratrol, and a combination thereof. In some embodiments, the second agent is selected from the group consisting of: CBD, THC, CBN, CBG, CBC, THCA, CBDA, THCV, and a combination thereof.

In some embodiments, the composition at therapeutically effective concentrations or dosages be combined with a pharmaceutically or pharmacologically acceptable carrier, excipient, or diluent, either biodegradable or non-biodegradable. For example, the composition may be administered in the pure form or in a pharmaceutically acceptable formulation including suitable elixirs, binders, and the like (also generally referred to a "carriers") or as pharmaceutically acceptable salts (e.g., alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil-based vehicles. Water may be used as the carrier for the preparation of compositions (e.g., injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc.). Solid diluents and excipients include lactose, starch, conventional disintegrating agents, coatings, and the like. Preservatives such as methylparaben or benzalkonium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

Examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly (malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropyl cellulose, hydroxypropyl-methylcellulose phthalate, noncrystalline cellulose, magnesium aluminum silicate, triethanolamine, polyvinyl alcohol, polyvinylpyrrolidone, sugars, and starches. See, for example, Gennaro, A. R. (1995) Remington: The Science and Practice of Pharmacy. 19th Edition, Mack Publishing Company, Easton.

In some embodiments, the chemicals can be purified and blended together to produce a formulation is capsule form. In these formulations, the active ingredient is dissolved in sesame seed oil or a similar oil and enclosed in a gel-capsule. In other embodiments, the formulation may be arranged to be used as an injectable or as an aerosol. In these embodiments, as will be apparent to one of skill in the art, the appropriate pharmaceutically acceptable additives may be added so that the pharmaceutical composition is in the appropriate form.

As will be appreciated by one knowledgeable in the art, the formulation may be used as, for example, an anti-emetic, appetite stimulant, or as a treatment for nausea, dementia, Alzheimer's disease, glaucoma, high blood pressure, inflammation, or multiple sclerosis.

Additional Ingredients

Cannabinoids are susceptible to oxidation and hydrolysis. Over time it is possible for cannabinoids to be exposed to oxygen, hydrogen ions (acids, water), in addition to any other environmental factors that will cause their degradation.

Organic bases can be used to prevent the degradation of the cannabinoids. These organic bases include, but are not limited to, butyl hydroxyl anisole (BHA), butyl hydroxyl toluene (BHT) and sodium ascorbate; at concentrations between 0.001 to 5%>w/w, for example. Organic bases such as the following can improve the stability of cannabinoids from chemical degradation for up to 2 years: BHA 0.001 to 5% w/w, BHT 0.001 to 5% w/w, and combinations of BHA and BHT can also be used.

Antioxidants can be used to prevent or at least inhibit or mitigate the degradation of cannabinoids from oxidation. Examples of antioxidants include: ethanol, polyethylene glycol 300, polyethylene glycol 400, propylene glycol, propylene carbonate, N-methyl-2-pyrrolidones, dimethylacetamide, dimethyl sulfoxide, hydroxypropyl-P-cyclodextrins, sulfobutylether-.beta.-cyclodextrin, a-cyclodextrin, HSPC phospholipid, DSPG phospholipid, DMPC phospholipid, DMPG phospholipid, ascorbyl palmitate, butylated hydroxyanisole, butylated hydroxyanisole, propyl gallate, a-tocopherol, .gamma.-tocopherol, propyl gallate, lecithin, Vitamin E tocopherol, sesamin, sesamol, sesamolin, alpha-tocopherol, ascorbic acid, ascorbyl palmitate, fumaric acid, malic acid, sodium metabisulfite and EDTA. Specific antioxidant examples include, but are not limited to, Ascorbic Acid: 0.001 to 5% w/w, Vitamin E Tocopherol: 0.001 to 5% w/w, Tocopherol: 0.001 to 5% w/w, and combinations of ascorbic acid, vitamin E tocopherol, and tocopherol can be used for this invention.

Chelating agents can prevent or at least mitigate the degradation of cannabinoids from metal ions in solution. Chelating agents include, but are not limited to, ethylenediaminetetraacetic acid (EDTA), phosphoric acid, polyphosphates, polysaccharides, citric acid, and any combination thereof.

Preservatives can be used to prevent microbial spoilage. These preservatives include: methylparabens, ethylparabens, propylparabens, butylparabens, sorbic acid, acetic acid, propionic acid, sulfites, nitrites, sodium sorbate, potassium sorbate, calcium sorbate, benzoic acid, sodium benzoate, potassium benzoate, calcium benzoate, sodium metabisulfite, propylene glycol, benzaldehyde, butylated hydroxytoluene, butylated hydroxyanisole, formaldehyde donors, essential oils, citric acid, monoglyceride, phenol, mercury components and any combination thereof. Specific examples include, but are not limited to, sodium benzoate and potassium sorbate.

Additionally, the pH can be lowered to prevent or retard microbial growth. Lowering the pH below 4.0 is sufficiently low enough to prevent microbial growth for a minimum of 1 month.

Preservatives and/or stabilizers can be added during formulation. Depending on the nature of the preservative/stabilizer, it may be contained in either the oil phase, interfacial layer, or the aqueous continuous phase. Once dissolved the preservatives and stabilizers are released into solution imparting their properties into the aqueous system.

EXAMPLES

Test (A)

Shake (cannabis product) for method A, B and C: This shake was used in methods A, B and C (Tests B, C and D). The shake had a THC content of 11.4 mg/g and a THCa content of 191.33 mg/g.

Test (B)

Butter method A: Control with no infusion of cannabis material to calibrate the testing machine.

Test (C)

Butter method B: This butter was produced using the typical "crock pot" method used by a high majority of home "weed butter" makers. This method has a substantially high transfer rate of cannabis "weed" flavors and odors into a lipid product. The method notably degrades the lipid compound causing a grainy texture that was not shelf stable at room temperature. The infusion rate for this process was 2.67 mg/g of THC with no inclusion of THCa. This method used 3.5 g of cannabis product for the infusion into 227 g of lipid compound.

Test (D)

Butter method C: This method uses the patent process described here. The test results show an inclusion of THC & THCa into the lipid compound. This method has an infusion rate of 1.66 mg/g of THC & 0.74 mg/g of THCa. Adding these 2 compounds (THC+THCa) together generates an infusion rate of 2.4 mg/g of total THC. This infusion rate is statistically the same as Butter method B (Test C) but with the inclusion of THCa. The infused lipid compound produced by this method did not demonstrate the substantial degrading effects found in the "crock pot" method. The lipid was shelf stable at room temperature, not grainy in texture and had a substantially reduced transfer of "weed" flavor and odor. This method used 3.5 g of cannabis product for the infusion into 227 g of lipid compound.

Test (E)

Shake SNLC-21 (cannabis product): This cannabis product was used as a follow up test of the described method in this patent. The cannabis product has a THC content of 2.02 mg/g and a THCa content of 132.31 mg/g.

Test (F)

Butter: This infused lipid product used log of Item E (Shake SNLC-21) for infusion into 227 g of a lipid compound. The increase in cannabis product from 3.5 g to log was performed to demonstrate the scalability of the infusion process while maintain the goals of the method. The process had an infusion rate of 17.08 mg/g of THC and 12.98 mg/g of THCa. The lipid compound was substantially stable at room temperature and was not substantially degraded when compared to the "crock pot" method, with a low transfer of "weed-like" flavor and odor.

CONCLUSION

The infusion rate of THC & THCa is a statistically equal when compared a traditional decarboxylation method of THC infusion only. The inclusion of THCa post decarboxylation for infusion into a lipid compound is novel and new. THCa has many unique purported health benefits, when combined with THC in one infusion, those purported benefits can be increased. The lipid compound exhibited no substantial degradation with stability at room temperature and a lower rate of odor and flavor transfer. The reduction in "weed" flavor and odor transfer into a lipid compound is new and novel for a decarboxylation process.

All publications, patents and patent applications cited herein, whether supra or infra, are hereby incorporated by reference in their entirety to the same extent as if each individual publication, patent, or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A method of preparing a cannabinoid infused lipid composition:
   a) providing cannabis;
   b) decarboxylating the cannabis by heating the cannabis to a temperature from 180° F. to 280° F., for a time which ensures that at least 90% conversion of one or more acid cannabinoids in the cannabis are converted to their neutral form, while ensuring that the thermal degradation of THC to CBN is less than 10% and wherein the cannabis has no more than 10% moisture to yield a decarboxylated cannabis;
   c) contacting an organic solvent with the decarboxylated cannabis, wherein the organic solvent is selected from the group consisting of ethanol, propanol, isopropanol, butanol, and mixtures thereof;
   d) extracting at least one bioactive molecule from the decarboxylated cannabis into the organic solvent, thereby producing a cannabis extract;
   e) contacting the cannabis extract with a lipid compound selected from the group consisting of dairy butters, canola oil, cocoa butter, coconut oil, corn oil, ghee, lard, nut butters, nut oils, olive oil, peanut oil, safflower oil, soybean oil, sunflower oil, vegetable oils, and mixtures thereof; and
   f) infusing at least one bioactive molecule from the cannabis extract into the lipid compound via a pressure infusion vessel, thereby producing a cannabinoid-infused lipid composition.

2. The method of claim 1, further comprising recovering the cannabinoid-infused lipid composition from the organic solvent; thereby producing an edible cannabis composition.

3. The method of claim 1, wherein the step of lipid infusion of the extracted and decarboxylated cannabis plant material-derived composition is performed at a pressure between 0 psi and 25 psi above atmospheric pressure.

4. The method of claim 1, wherein the cannabinoids are selected from the group consisting of tetrahydrocannabinolic acid (THCA), cannabidiolic acid (CBDA), cannabichromenic acid (CBC) and mixtures thereof.

5. The method of claim 1, wherein the organic solvent is an alcohol having a concentration of 10% to 50%.

6. The method of claim 1, further comprising the step of: winterization and/or de-waxing of the cannabis extract.

7. The method of claim 1, wherein the cannabinoid-infused lipid composition is used in the preparation of food products.

8. The method of claim 1, wherein steps (b) or (d) are repeated at least once.

* * * * *